United States Patent
Johnson

(10) Patent No.: US 7,652,190 B2
(45) Date of Patent: Jan. 26, 2010

(54) INTEGRATED WOUND DRESSING SYSTEM

(75) Inventor: Ross A. Johnson, Anderson, SC (US)

(73) Assignee: Tactical Medical Solution, Inc., Anderson, SC (US)

( * ) Notice: Subject to any disclaimer, the term of this patent is extended or adjusted under 35 U.S.C. 154(b) by 0 days.

(21) Appl. No.: 11/737,096

(22) Filed: Apr. 18, 2007

(65) Prior Publication Data

US 2007/0260166 A1 Nov. 8, 2007

Related U.S. Application Data

(60) Provisional application No. 60/746,539, filed on May 5, 2006, provisional application No. 60/822,198, filed on Aug. 11, 2006.

(51) Int. Cl.
- A61F 15/00 (2006.01)
- A61F 13/06 (2006.01)
- A61F 13/00 (2006.01)
- A61F 13/02 (2006.01)
- A61B 17/00 (2006.01)
- A61B 17/08 (2006.01)
- A61B 17/04 (2006.01)

(52) U.S. Cl. .............. 602/48; 602/49; 602/50; 602/51; 602/52; 602/56; 602/57; 602/58; 602/59; 602/72; 604/304; 604/305; 604/306; 604/307; 604/308; 606/201; 606/203; 606/204; 606/213; 606/215; 606/216; 606/232; 606/293; 606/304; 606/305; 600/572; 600/571

(58) Field of Classification Search .......... 602/48–52, 602/56–59, 72; 604/304, 305, 306, 307, 604/308; 606/201, 203, 204, 213, 215, 216, 606/232, 293, 304, 305; 600/572, 571

See application file for complete search history.

(56) References Cited

U.S. PATENT DOCUMENTS

| | | | | |
|---|---|---|---|---|
| 2,133,609 A | * | 10/1938 | Eustis | 602/42 |
| 3,491,753 A | * | 1/1970 | Brockenshaw et al. | 602/46 |
| 4,085,746 A | | 4/1978 | Castiglia | |

(Continued)

OTHER PUBLICATIONS

Definition of wrap.*

(Continued)

*Primary Examiner*—Patricia Bianco
*Assistant Examiner*—Tarla R Patel
(74) *Attorney, Agent, or Firm*—Cahn & Samuels LLP

(57) ABSTRACT

An integrated wound dressing system and method including a bandage and a self-contained receptacle that stores treatment material for the care and treatment of wounds. The treatment material is easily accessible and can be removed from the receptacle through an exit. The treatment material can then be used to control bleeding and/or clean the wound before dressing. The bandage may include a layer of plastic that acts as an occlusion barrier to reduce heat loss and maintain moisture levels at the wound site. The occlusion barrier also acts to prevent the passage of air into or out of the wound site. The bandage also includes fasteners that act to prevent unintentional unraveling and to secure the bandage during final packaging. These fasteners help facilitate the wrapping of amputations, stumps, and extremities. The integrated wound dressing system provides an all-in-one system for treating and dressing wounds and reduces the time required to do so.

35 Claims, 15 Drawing Sheets

U.S. PATENT DOCUMENTS

| | | | |
|---|---|---|---|
| 4,748,978 A * | 6/1988 | Kamp | 424/445 |
| 4,926,848 A | 5/1990 | Shimkus et al. | |
| 5,480,377 A * | 1/1996 | Cartmell et al. | 602/48 |
| 5,538,500 A * | 7/1996 | Peterson | 602/48 |
| 5,722,943 A * | 3/1998 | Sessions | 602/57 |
| 5,891,078 A * | 4/1999 | Turngren et al. | 602/58 |
| 6,296,618 B1 | 10/2001 | Gaber | |
| 6,545,193 B1 | 4/2003 | Morgenstern | |
| 6,573,419 B2 | 6/2003 | Naimer | |
| 6,719,710 B2 | 4/2004 | Darcey | |
| 6,762,338 B2 | 7/2004 | Harder | |
| 6,982,359 B1 * | 1/2006 | Beaudry | 602/54 |
| 2002/0128579 A1 | 9/2002 | Church | |
| 2003/0149389 A1 | 8/2003 | Daneshvar | |
| 2005/0256439 A1 * | 11/2005 | Grossman | 602/57 |
| 2006/0163101 A1 * | 7/2006 | Assie et al. | 206/440 |

OTHER PUBLICATIONS

Definition of wrap and attached.*

* cited by examiner

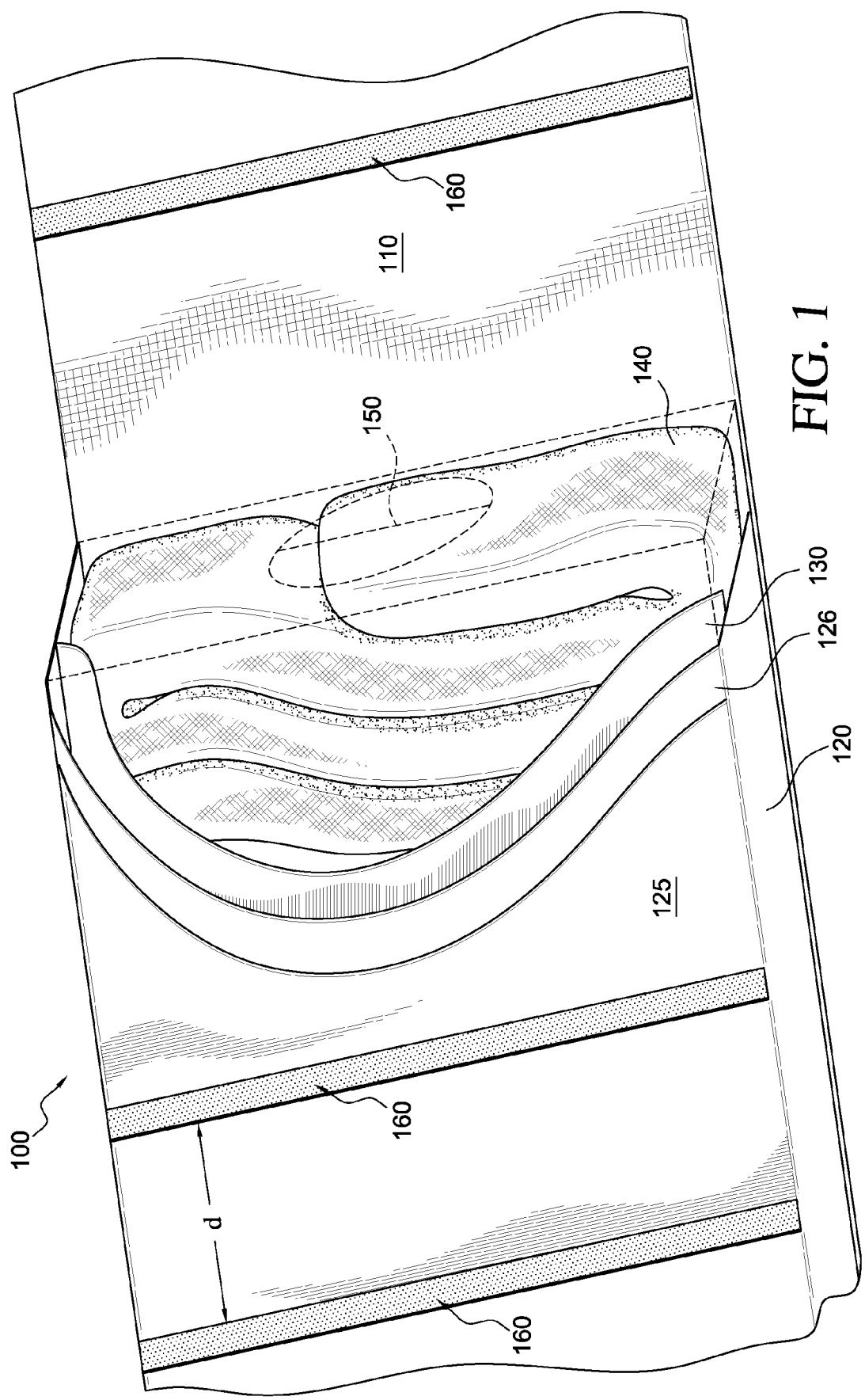

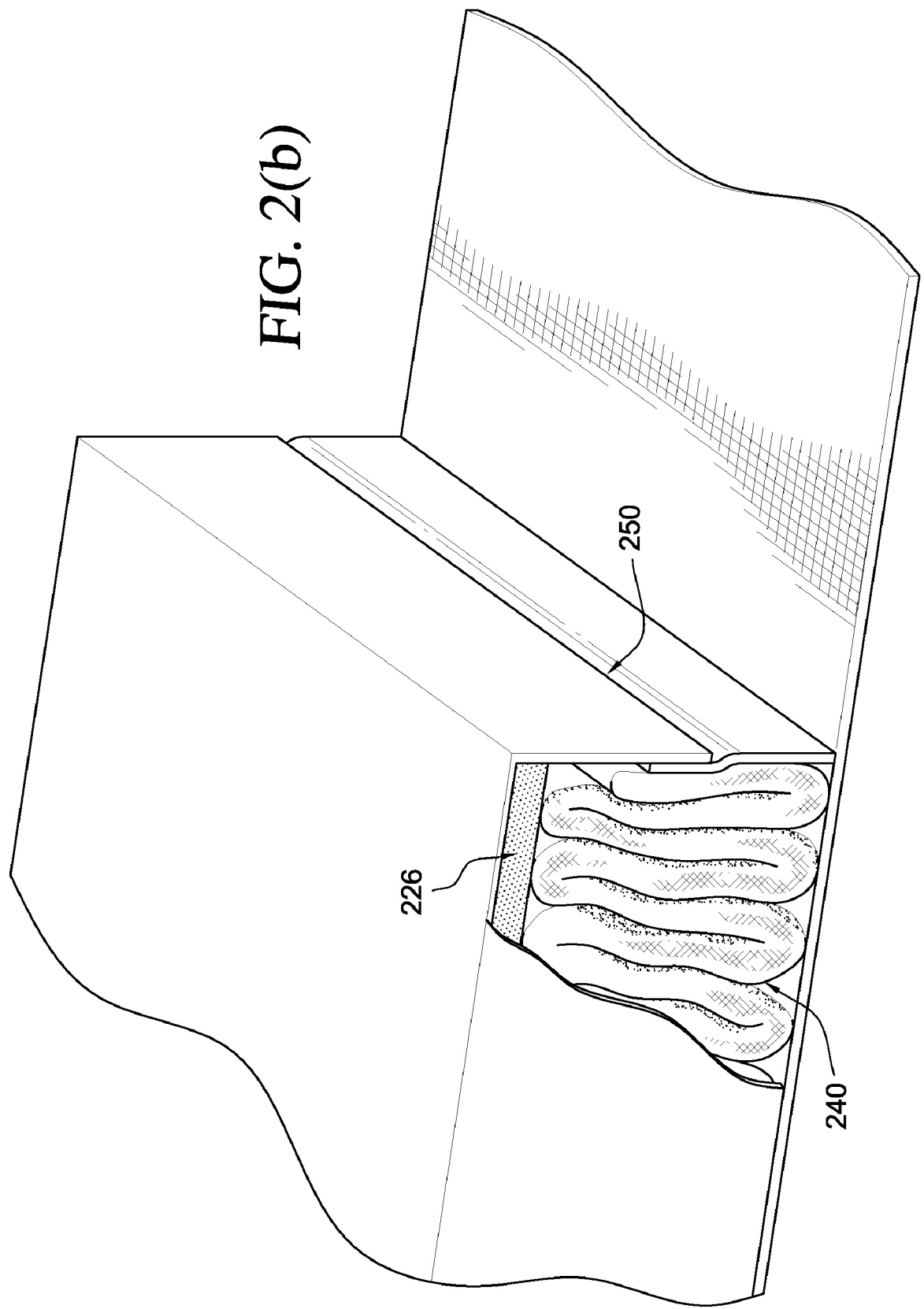

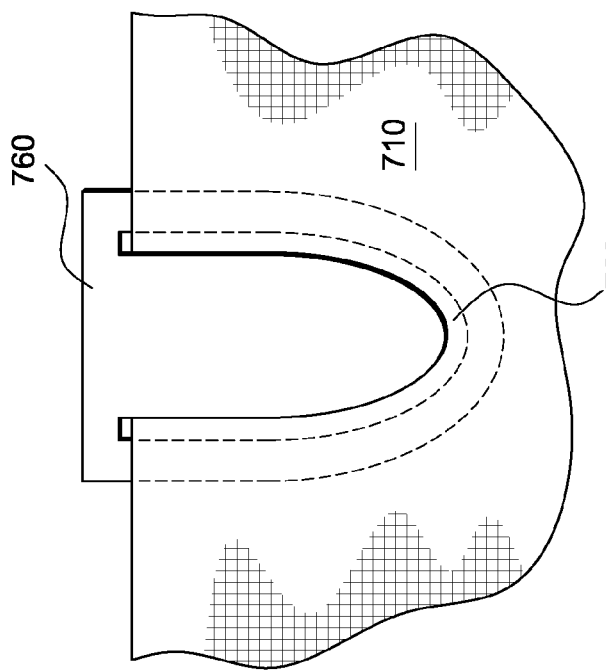
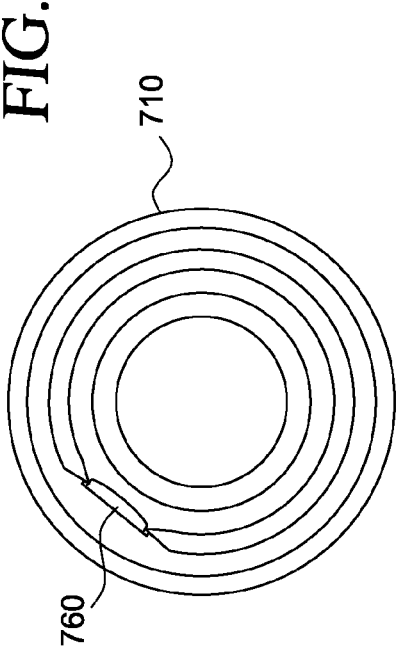
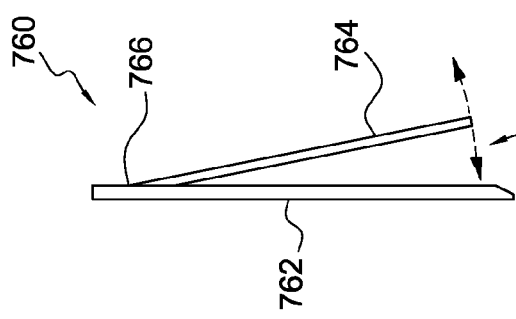
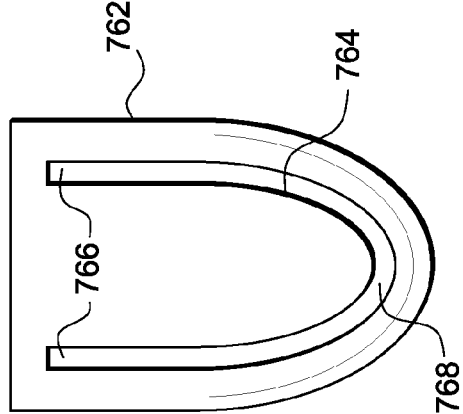
FIG. 7(a)
FIG. 7(b)
FIG. 7(c)
FIG. 7(d)

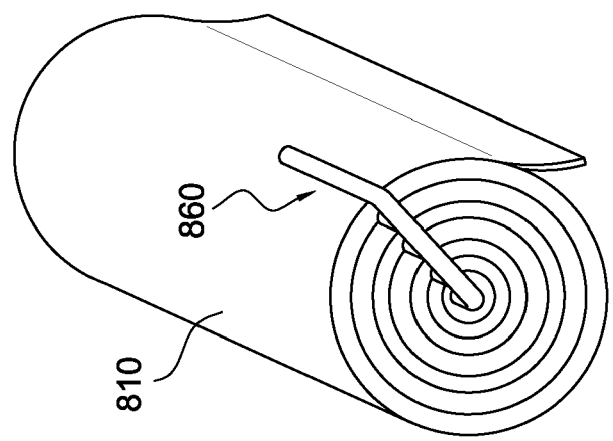
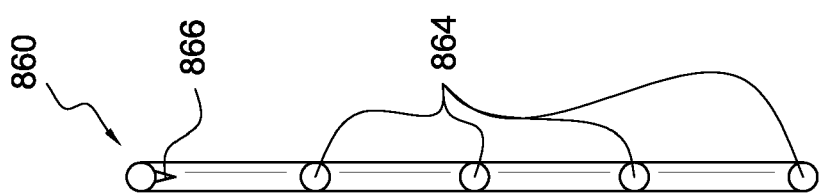
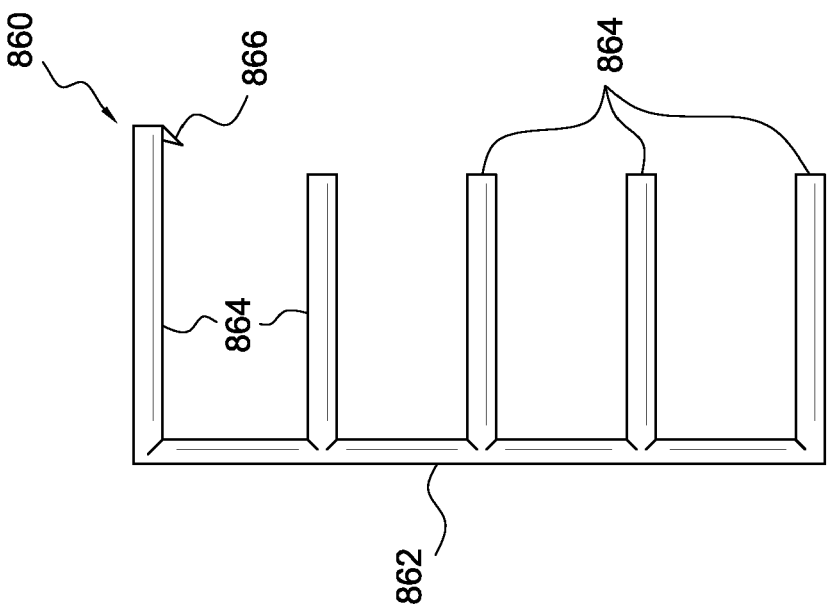
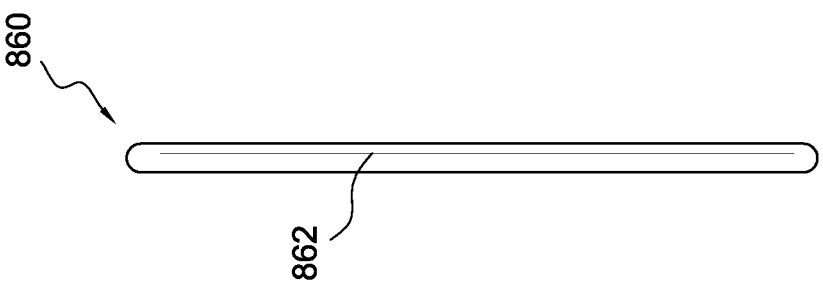
FIG. 8(d)
FIG. 8(c)
FIG. 8(a)
FIG. 8(b)

US 7,652,190 B2

INTEGRATED WOUND DRESSING SYSTEM

I. CROSS REFERENCE TO RELATED APPLICATION

This application claims the benefit of U.S. Provisional Patent Application No. 60/746,539, filed May 5, 2006, which is incorporated herein by reference.

This application claims the benefit of U.S. Provisional Patent Application No. 60/822,198, filed Aug. 11, 2006, which is incorporated herein by reference.

II. FIELD OF THE INVENTION

The present invention relates to an integrated wound dressing system for the care and treatment of wounds. More particularly, the present invention relates to an all-in-one wound dressing system and method having a bandage, treatment material, and fasteners in an integrated unit for quickly and effectively treating a wide array of wounds.

III. BACKGROUND OF THE INVENTION

One of the leading causes of death on military battlegrounds and in hospital trauma units is severe blood loss and the associated shock that it produces. Therefore, one of the most vital priorities of caregivers (medics, first responders, and medical providers) is to control and stop bleeding. There are many devices and methods that may be employed to control bleeding. One of the most commonly used devices for bleeding control is the elastic bandage.

Elastic bandages have been known in the prior art for many years. These bandages are sometimes called "roller" bandages or "wraps" and come in rolls having various fasteners, such as Velcro®, metal clips, or tape. They are sold under brand names such as ACE® wrap.

Elastic bandages are a preferred wound dressing by caregivers ranging from physicians and trained medics to individual first responders with minimal first aid training. Elastics bandages are highly adaptable to treat a range of wounds and conform to virtually any body part. Elastic bandages provide many benefits at the wound site, including applying varying degrees of compression and support to the wound, as well as providing a sterile barrier around the wound. Compression and support is effective in controlling bleeding, and reducing pain and swelling in the area around the wound. The sterile barrier reduces the risk of contamination and infection of the wound.

Elastic bandages are also effective in applying and securing other treatment medicaments and materials to the wound site. One material that is often used in wound dressing and treatment is a woven fabric or gauze. Gauze is effective in controlling bleeding and can be placed directly on the wound to provide focused treatment at the wound site. Gauze is also used as a sterile material to remove foreign matter from the wound site.

Many currently available bandages act to cover the wound site. Their main function is to keep the wound site clean, not to control hemorrhage. In order to control hemorrhage, another material, such as gauze, must be used at the wound site. The gauze can then be covered and wrapped by the bandage. These bandages require the introduction and use of other materials to properly treat a wound.

There are presently available hemostatic dressings that are designed to promote the accelerated clotting of blood at wounds. Examples of these dressing are the HemCon® bandage (HemCon Inc., Tigard, Oreg., U.S.A) and QuickClot® (Z-Medica Corporation, Wallingford, Conn., U.S.A.). While these products generally promote clotting, they still require the application of direct pressure to the wound site in order to be effective.

While the above described wound treatments are suitable, the handling and use of the various separate components can be cumbersome and time consuming which increases the risk of blood loss and associated complications. Also, the introduction of multiple components to the wound site increases the risk of contamination and infection. Notwithstanding the usefulness of the above-described treatments, a need still exists for a fully integrated wound treatment system and method for treating wounds quickly and effectively while reducing the risk of contamination and infection.

IV. SUMMARY OF THE INVENTION

In accordance with an embodiment of the invention, a wound dressing system, comprising a wrap; a receptacle disposed on said wrap; and, a treatment material disposed inside said receptacle, said receptacle including an exit to facilitate removal of said treatment material.

In accordance with another embodiment of the invention, an integrated wound dressing system, comprising a bandage suitable for dressing a wound; a receptacle disposed on said bandage, said receptacle comprising a wound surface including a layered structure; at least one pressure member in communication with said bandage; and, a treatment material disposed inside said receptacle, said receptacle including an exit to facilitate removal of said treatment material.

In accordance with yet another embodiment of the invention, a method of applying the wound dressing system to a wound, comprising removing the treatment material from the receptacle; contacting the wound with the treatment material; and, contacting the treatment material with the wrap.

In accordance with still another embodiment of the invention, a method of applying the wound dressing system to a wound, comprising removing the treatment material from the receptacle; applying the treatment material to the wound; applying the pressure member to the wound via the treatment material; and, applying the bandage to the wound via the pressure member.

V. BRIEF DESCRIPTION OF THE DRAWINGS

The present invention is described with reference to the accompanying drawings. In the drawings, like reference numbers indicate identical or functionally similar elements.

FIG. 1 illustrates a cut away view of an exemplary embodiment of the integrated wound treatment system in accordance with the present invention.

FIG. 2(b) illustrates a cut away view of the embodiment of the integrated wound treatment system illustrated in FIG. 2(a).

Figure 4A:
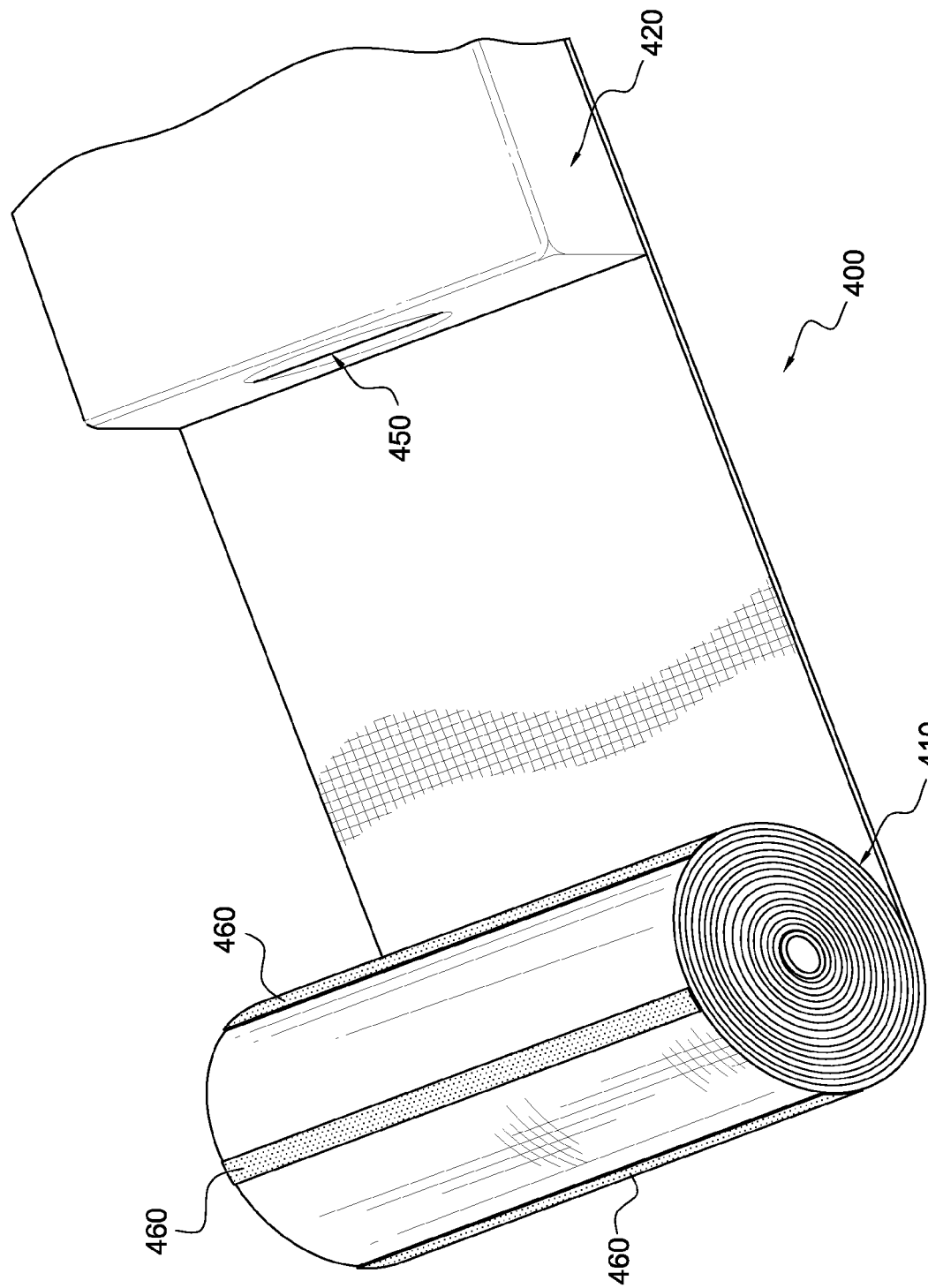
Figure 4B:
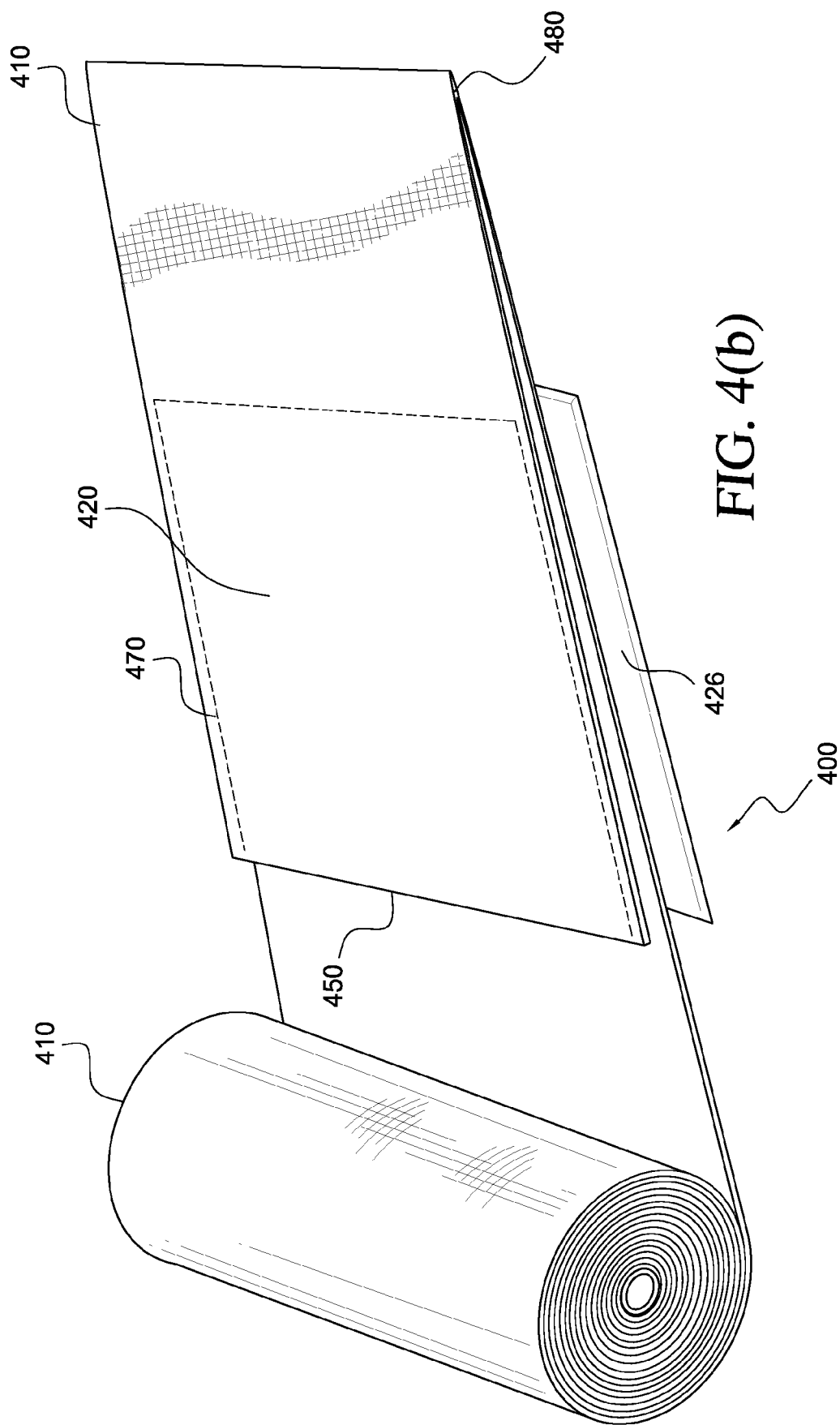

FIGS. 4(a)-(b) illustrate perspective views of embodiments of the integrated wound treatment system in accordance with the present invention.

Figure 5A:
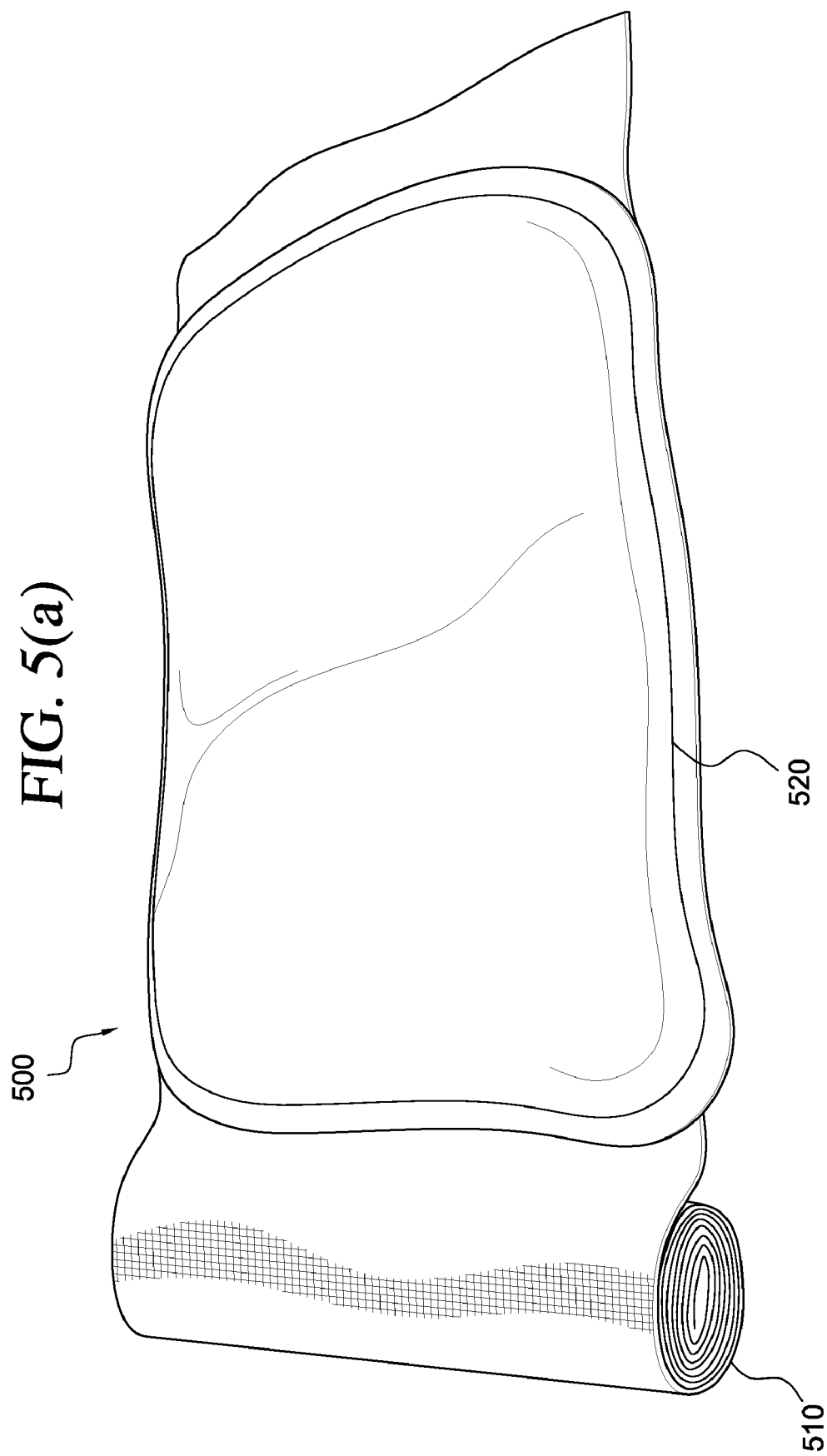
Figure 5B:
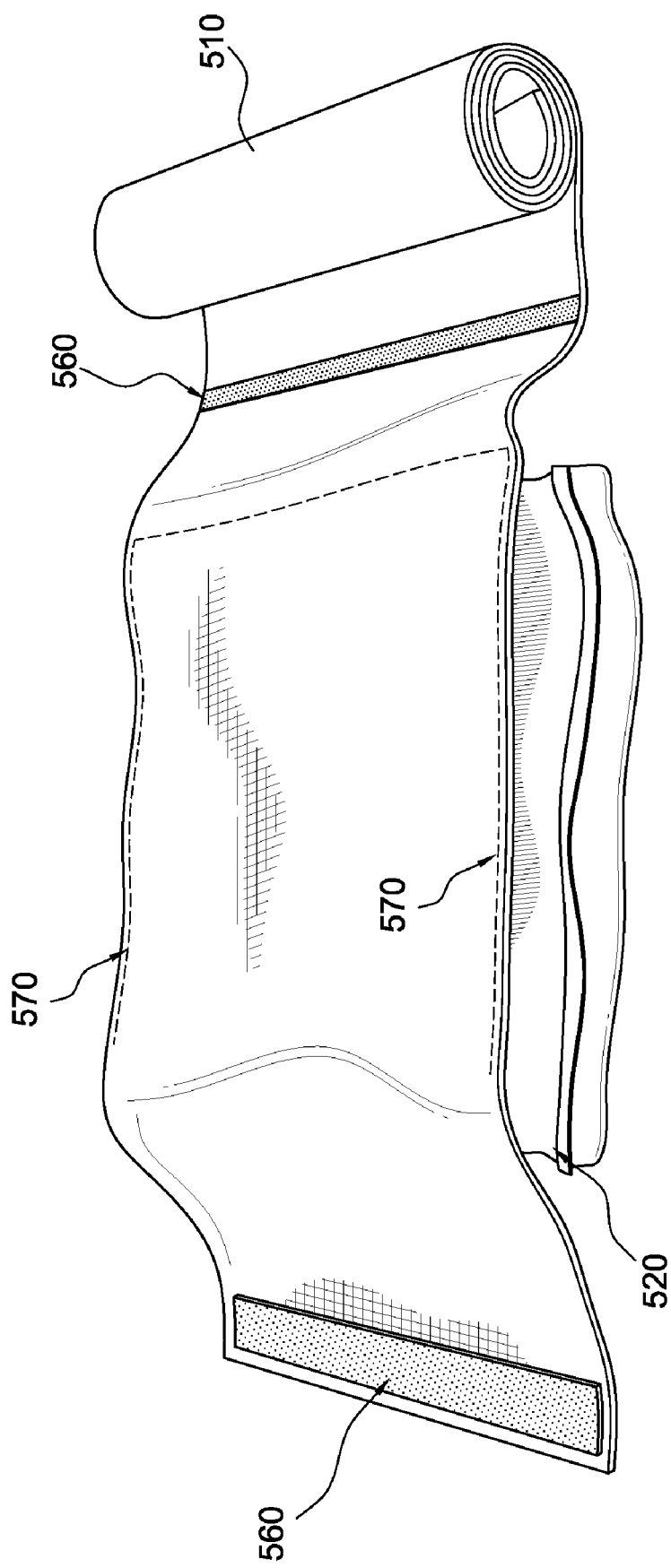
Figure 5C:
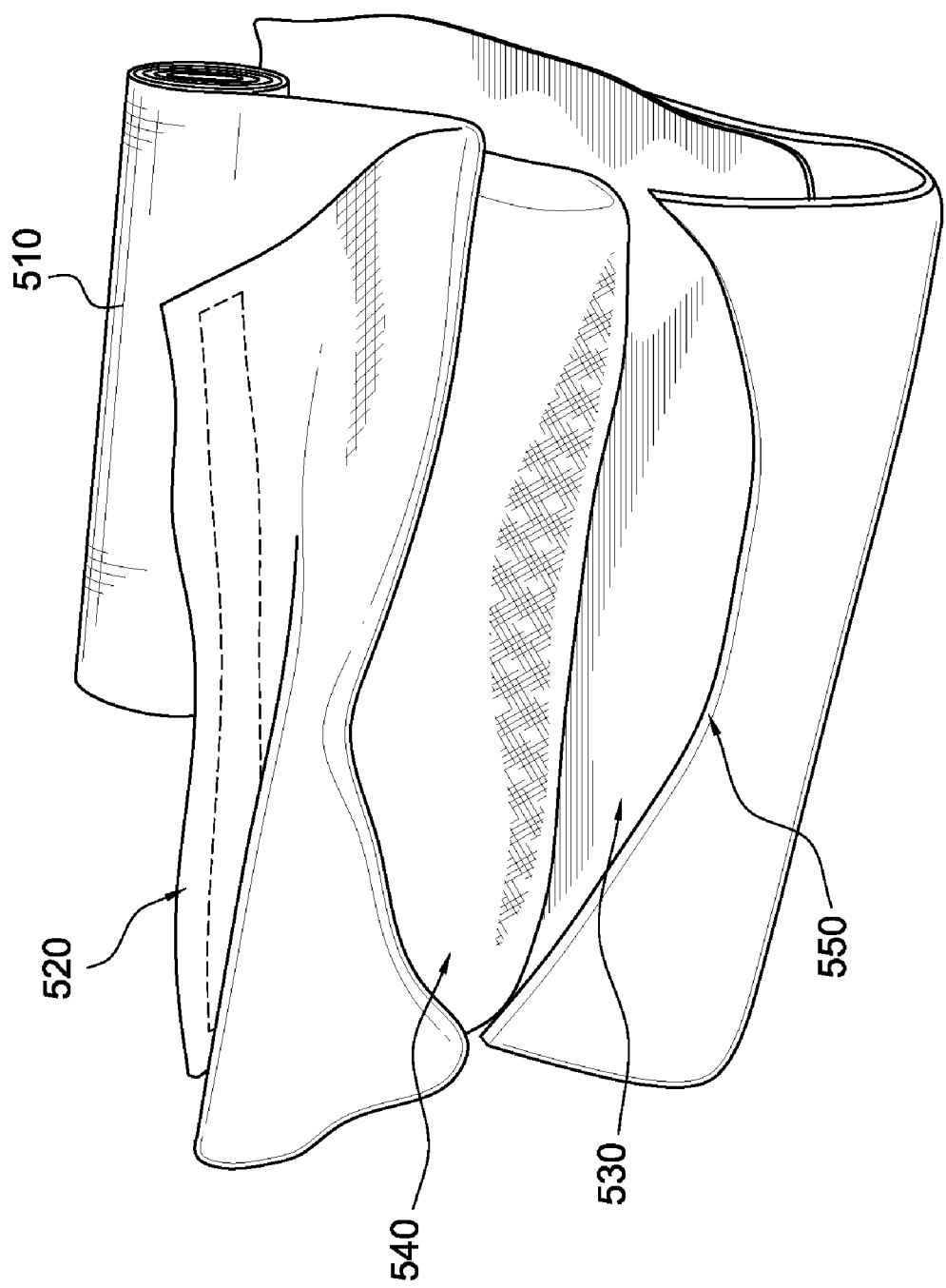

FIGS. 5(a)-(c) illustrate exemplary embodiments of the integrated wound treatment system, including receptacle, in accordance with the present invention.

FIGS. 6(a)-(d) illustrate exemplary embodiments of a pressure member that may be used with the present invention.

FIGS. 7(a)-(d) illustrate exemplary embodiments of a fastener that may be used with the present invention.

FIGS. 8(a)-(d) illustrate exemplary embodiments of a fastener that may be used with the present invention.

Given the following enabling description of the drawings, the apparatus should become evident to a person of ordinary skill in the art.

VI. DETAILED DESCRIPTION OF THE DRAWINGS

The present invention as illustrated, for example, in FIG. 1 is directed to an integrated wound treatment system ("system") 100. The system 100 preferably includes at least an elastic bandage 110 and a receptacle (or means for storing sterile material and/or gauze) 120 disposed on the elastic bandage 110.

In preferred embodiments of the invention, the receptacle 120 forms a pocket and contains a sterile wound treatment material 140, e.g. gauze. The receptacle 120 includes a first surface 125 adapted for contact with the wound. The surface may comprise a single layer structure or a multiple layer structure. In one embodiment, the surface includes a non-adherent pad layer 126, a plastic layer 130, or a combination thereof. For example, in accordance with an aspect of the invention, the non-adherent pad 126 is disposed on an exterior surface of the receptacle 120 and forms a wound contacting surface 125.

In keeping with the invention, the wound treatment system 100 is provided with an occlusion layer. For example, the plastic layer 130 is disposed adjacent to the non-adherent pad 126. In some embodiments, plastic layer 130 is disposed adjacent an interior surface of receptacle 120. In some embodiments, the plastic layer 130 can be removed from receptacle 120 and placed on the wound such that the plastic layer 130 forms the wound contacting surface. Alternatively, if desired, the plastic layer 130 can be removed from the receptacle and discarded such that no occlusion layer is provided. In some embodiments, the plastic layer 130 may be fixedly attached to the wound contacting surface 125 such that when the dressing is applied, plastic layer 130 abuts the wound and forms an occlusion layer. The plastic layer 130 acts to maintain moisture and heat levels at the wound site and impedes the passage of air into or out of the wound site.

The non-adherent pad layer 126 minimizes the adhesion of the dressing to the wound. The plastic layer 130 serves as an occlusion layer and protects the treatment material 140 from contamination. The occlusion layer is effective to provide a heat barrier that minimizes heat loss at the wound site. This is particularly useful when dressing abdominal wounds which often lead to significant heat loss. Occlusion dressings have also been found to promote faster healing.

The receptacle 120 includes an exit 150 that provides access to the treatment material 140 and facilitates controlled withdrawal of treatment material 140. The exit 150 may include any element, or combination of elements, that allow for the removal of the treatment material 140 from the receptacle 120. For example, the exit 150 may comprise any of a slit, an opening, an overlapping flap, or any similar arrangement that allows the treatment material 140 to be controllably removed from the receptacle 120. See FIGS. 1 and 2(b).

The receptacle 120 preferably has a low-profile design and provides a substantially flat pocket having a generally uniform distribution of treatment material 140 throughout the receptacle. The receptacle 120 and treatment material 140 are configured to store a sufficient amount of treatment material 140 to clean and treat a range of wound sizes and severities. The caregiver removes the treatment material 140 from the receptacle 120 by pulling the treatment material 140 through the exit 150. The desired amount of treatment material 140 may be readily selected by the caregiver. This is beneficial when treating multiple wounds, for example both entry and exit wounds, with the same dressing. In some embodiments, the treatment material 140 may be divided into portions of predetermined size, for example, with a perforated boundary between portions.

Once selected, the treatment material 140 is used to provide sterile cleaning of the wound. If no cleaning is necessary, or if controlling the bleeding is more vital, the treatment material 140 is placed on the wound, as needed. The elastic bandage 110 is then placed over the wound area and the wound is wrapped. The elastic bandage 110 may be wrapped such that it provides the desired compression to the wound in order to assist in bleeding control. In accordance with an aspect of the invention, the treatment material 140 may include a blood coagulant to provide additional control of bleeding. Exemplary coagulants include Chitosan, Fibrinogen and Thrombin.

In keeping with the invention, the elastic bandage 110 may also include fasteners or brakes 160 provided on at least one surface. The fasteners 160 are provided to assist with application of the bandage 110 and to minimize the unintentional unraveling of the bandage 110 during application. The fasteners 160 also facilitate securing the bandage 110 during final packaging. The fasteners 160 may include a variety of suitable fasteners that are applied in a variety of configurations. For example, the fasteners 160 may include a plurality of spaced apart Velcro® or adhesive strips 160, as shown in FIG. 1. The fasteners 160 may be disposed on the bandage 110 only, on the receptacle 120 only, or on both the bandage 110 and receptacle 120. Each fastener 160 may be spaced from adjacent fasteners 160 by a distance d, which distance can be up to several inches. Alternatively, the distance between fasteners 160 may vary. Also, see fasteners 160 in FIG. 4(a).

In accordance with the present invention, the treatment material 140 and exit 150 may be variously configured. In the embodiment shown in FIG. 1, the receptacle 120 includes an exit 150 comprising a slit. The treatment material 140 is packaged in the receptacle 120 in an s-shaped configuration with the end of the treatment material 140 abutting exit 150. The treatment material 140 may be pulled through the exit 150 by the caregiver during application. The treatment material 140 may be removed in an amount selected by the caregiver and used as needed, either to clean and/or pack the wound.

Figure 2A:
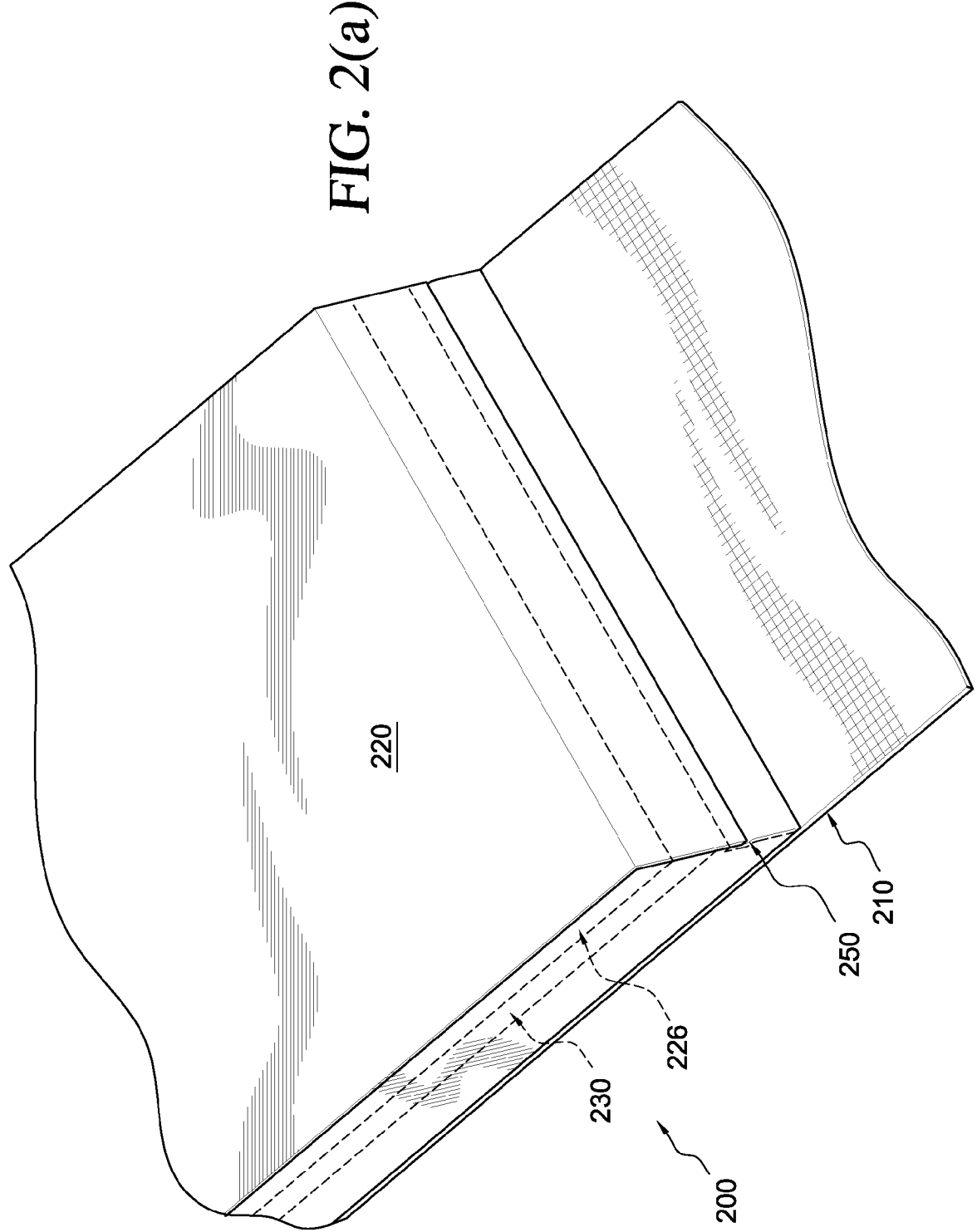
FIG. 2(a) illustrates a perspective view of an embodiment of the integrated wound treatment system in accordance with the present invention.

In the configuration shown in FIG. 2(a), the receptacle 220 includes an exit 250 formed by an overlapping flap that extends over the width of the receptacle 220. The treatment material (not shown) is packaged inside the receptacle 220 and removed from the receptacle through the overlapping flap 250, as needed. Receptacle 220 may also include non-adherent pad 226 and a plastic layer 230.

FIG. 2(b) illustrates a cut away view of the present invention as shown in FIG. 2(a). This view more clearly illustrates the packaged treatment material 240 inside the receptacle 220. The treatment material 240 is packaged in an accordion fold where the end of the material 240 abuts the overlapping flap. Consequently, the end of the treatment material 240 can be readily removed from the receptacle 220 by the caregiver through the overlapping flap 250.

Figure 3B:
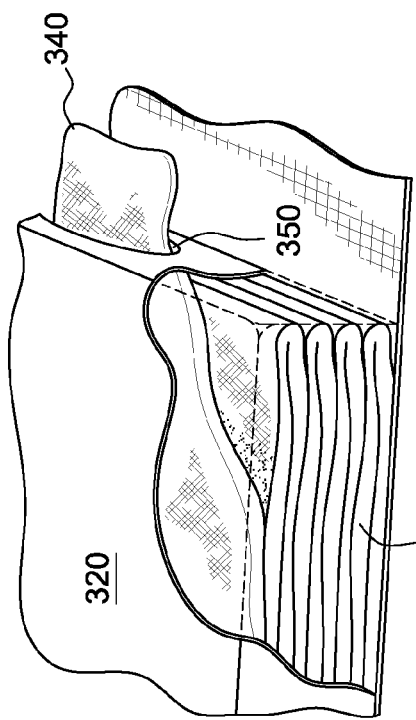
FIG. 3(b) illustrates a cut away view of an aspect of the exit and packaging configuration of the present invention.
Figure 3D:
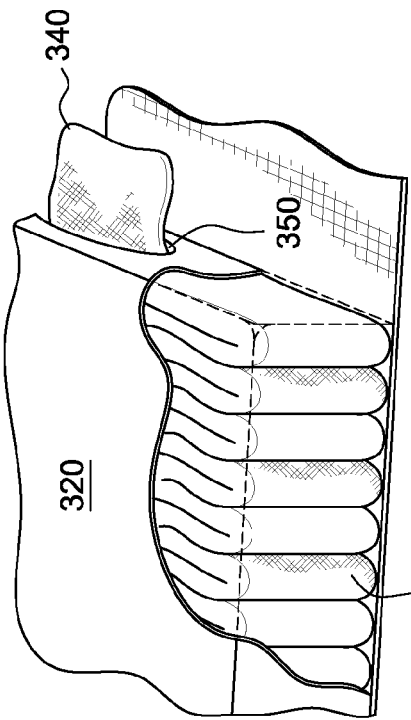
FIG. 3(d) illustrates a cut away view of an aspect of the exit and packaging configuration of the present invention.
Figure 3A:
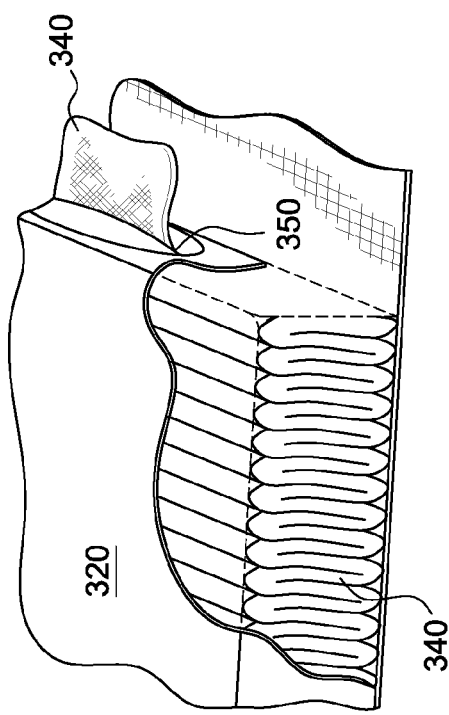
FIG. 3(a) illustrates a cut away view of an aspect of the exit and packaging configuration of the present invention.
Figure 3C:
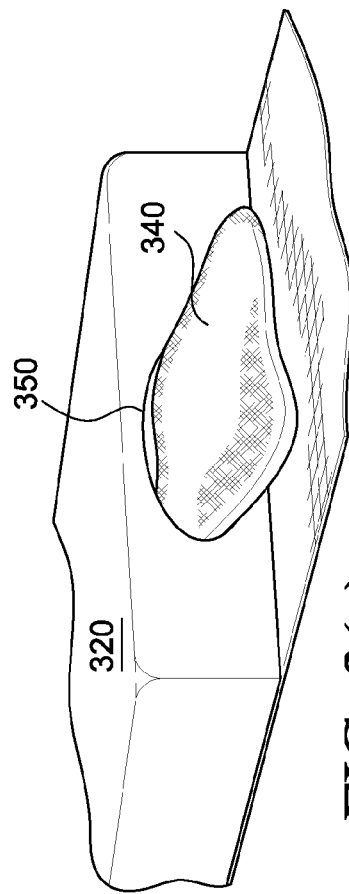
FIG. 3(c) illustrates a cut away view of an aspect of the exit and packaging configuration of the present invention.

FIGS. 3(a)-(d) illustrate various packaging configurations of the treatment material 340 of the present invention. FIG. 3(a) illustrates the treatment material 340 packaged inside the receptacle 320 in an accordion-folded configuration with an end slightly protruding from exit 350. FIG. 3(b) illustrates the treatment material 340 packaged inside the receptacle 320 in a top-folded configuration with an end slightly protruding from exit 350. FIG. 3(c) illustrates the treatment material 340 packaged inside the receptacle 320 and removed from the receptacle through exit 350. The material 340 is shown being removed in a flat-rolled configuration. FIG. 3(d) illustrates the treatment material 340 packaged inside the receptacle 320 in an s-folded configuration. In each case, the end of the treatment material 340 extends from the receptacle through exit 350.

In another embodiment of the present invention, as illustrated in FIG. 4(a), the integrated wound treatment system 400 includes a rolled elastic bandage 410 having a receptacle 420 disposed on the bandage. The receptacle 420 may be a pocket formed of a resilient material, such as foil or plastic. In accordance with an aspect of this embodiment, exit 450 may be positioned to face the rolled portion of bandage 410. Such an arrangement may simplify and accelerate application of the wound treatment system. Alternatively, exit 450 may face away from the rolled portion of bandage 410.

The rolled bandage 410 also includes fasteners 460 placed on the bandage 410. As illustrated in FIG. 4(a), a plurality of fasteners 460 are disposed on the exposed or exterior surface of bandage 410 in spaced relationships to each other. In accordance with the invention, fasteners 460 may be disposed on bandage 460 on the interior surface, the exterior surface or both surfaces, and may be placed in a variety of orientations. For example, in one embodiment, the fasteners 460 begin a few inches from the receptacle 420 and are placed every few to several inches over at least a portion of the bandage and in some embodiments over the length of the bandage.

In another embodiment of the present invention, as illustrated in FIG. 4(b), the integrated wound treatment system 400 includes a rolled elastic bandage 410 having a receptacle 420 disposed on the bandage. The receptacle 420 may be formed by folding the bandage 410 onto itself to create a pocket. The pocket may be formulated by, e.g., stitching the folded portion of the bandage as illustrated by stitches 470 while maintaining an opening 450 on at least one side. The pocket may be positioned adjacent a wound pad 426 disposed on the bandage 410. Treatment material, such as gauze and/or occlusive plastic sheeting, may be disposed inside the receptacle 420 to treat the wound.

In another exemplary embodiment of the present invention, as illustrated in FIGS. 5(a)-(c), the integrated wound treatment system 500 includes a rolled elastic bandage 510 and a sealed receptacle 520 having treatment material 540 packed inside, e.g. hemostatic gauze. The bandage 510 and receptacle 520 may embody many sizes and orientations, including a receptacle 520 that is separate and detached from the bandage 510, as shown in FIG. 5(a), a receptacle 520 having stitches 570 affixing it to the bandage 510, as shown in FIG. 5(b), or a receptacle 520 that is removably attached to the bandage 510, for example by Velcro®. The receptacle 520 may be made of a resilient material or gauze and may include removable gauze 540, removable occlusive plastic sheeting 530, and a closure flap or exit 550, as shown in FIG. 5(c). The receptacle 520 is opened just prior to use and the hemostatic gauze 540 is removed from inside the receptacle 520 and applied directly to the wound. The receptacle 520 and/or occlusive plastic sheeting 530 may be optionally placed over the gauze 540 to provide an occlusion layer. The elastic bandage 510 is then placed over the wound area and the wound is wrapped. The elastic bandage 510 may be wrapped such that it provides the desired compression to the wound in order to assist in bleeding control. The bandage may also include optional Velcro® and/or adhesive strips 560 to assist in wrapping and securing the bandage 510, as shown in FIG. 5(b).

To assist in providing compression to the wound, the wound treatment system may include a member, i.e. a structural element about which the bandage may be wrapped to increase pressure on the wound. FIGS. 6(a)-(d) illustrate exemplary embodiments of a pressure bar or member that may be used with the present invention. The pressure bar 600 is designed to have sufficient rigidity and may also have various surface shapes, including assorted protrusions and flat surfaces. The pressure bar 600 may be utilized along with the bandage 610 to apply an additional degree of pressure to the wound. This additional pressure is instrumental in providing extra control of bleeding at the wound site.

Figure 6A:
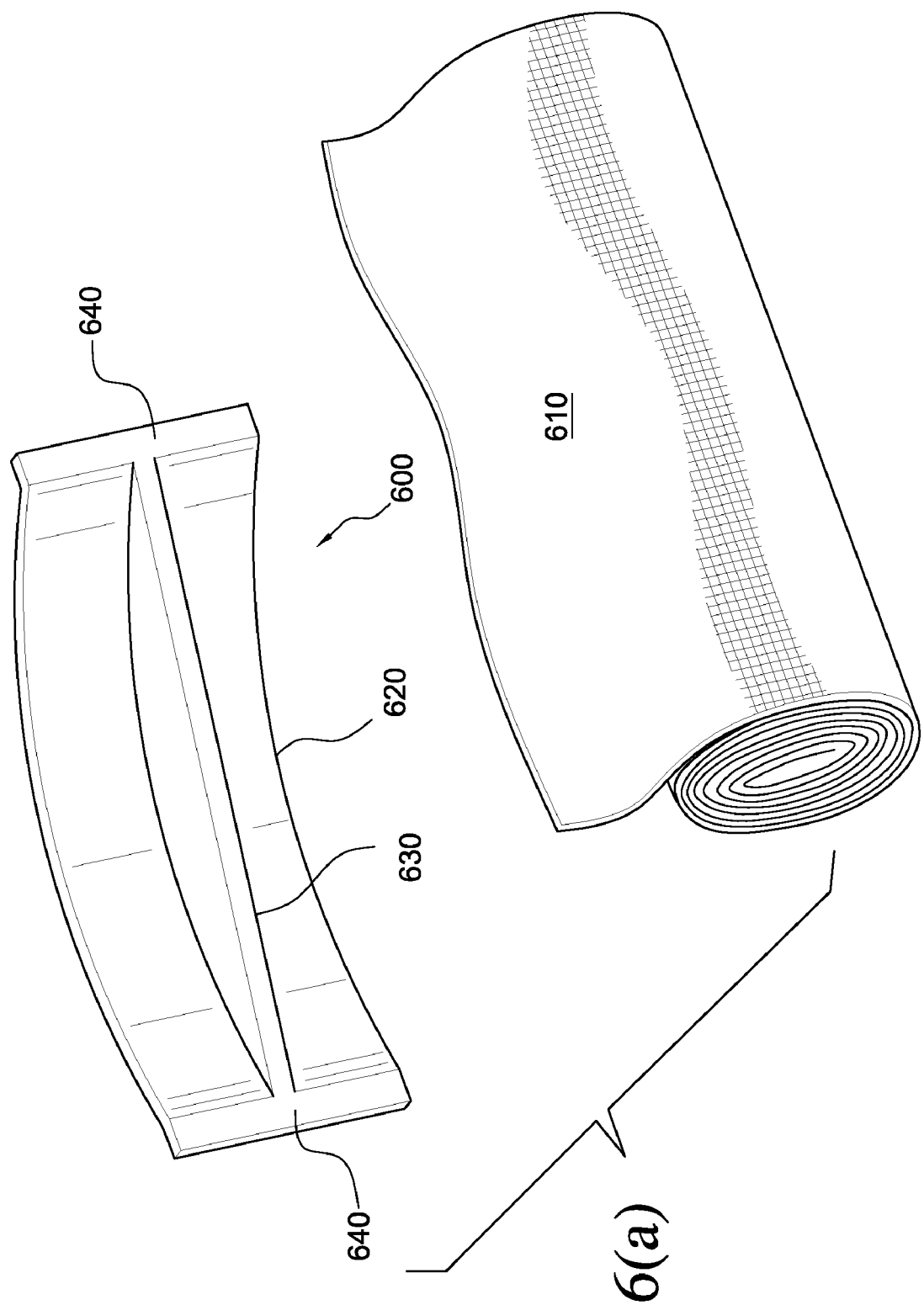
Figure 6B:
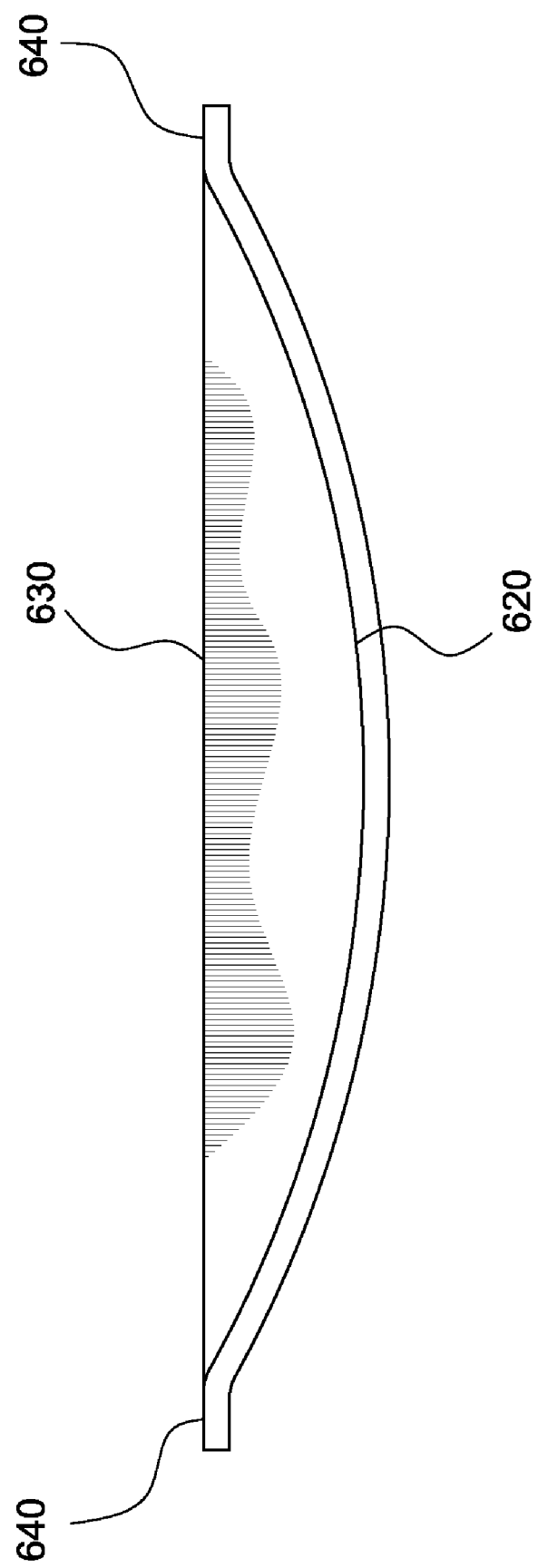
Figure 6C:
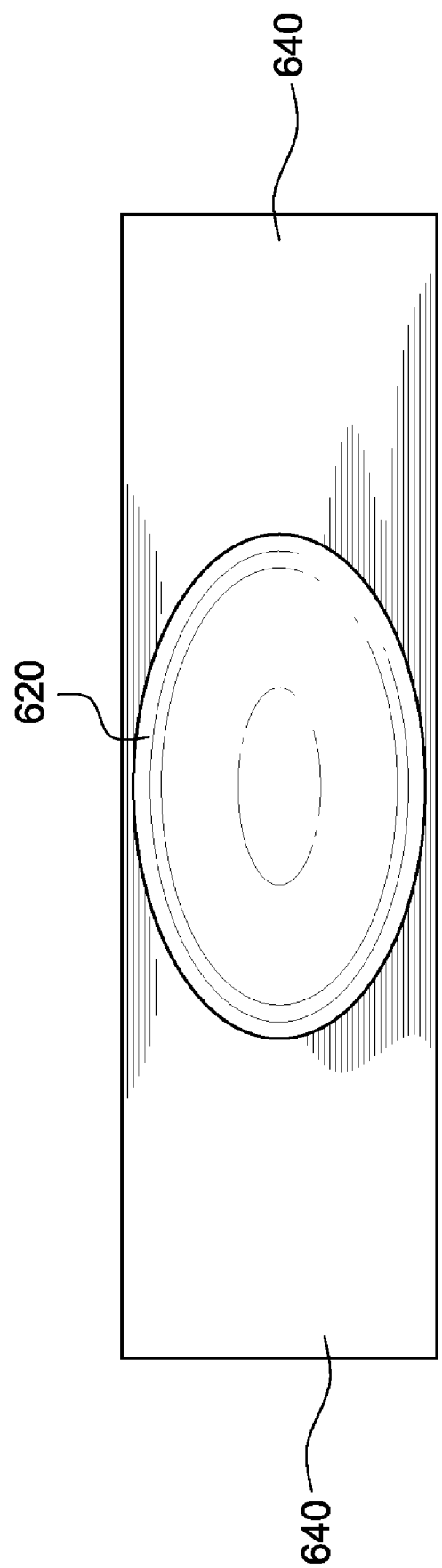
Figure 6D:
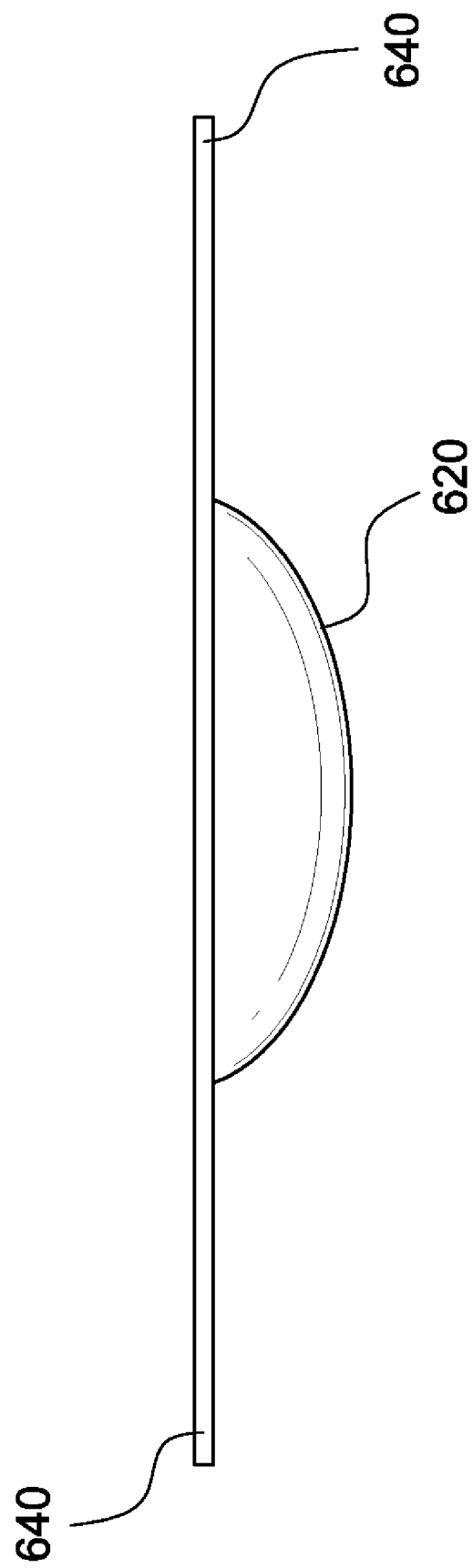

The pressure bar 600, as shown in FIGS. 6(a)-(b), is made of a length of resilient material having a protrusion 620 in the form of an arcuate or curved surface. The pressure bar 600 may also include a brace 630 that extends the length of the protrusion. The brace 630 provides additional support and rigidity to the protrusion 620 and allows the pressure bar 600 to maintain its shape and effectively provide pressure to the wound. The pressure bar 600, as shown in FIGS. 6(c)-(d), may also have a protrusion 620 in the form of a bowl-like surface. This embodiment may optionally include a brace, not shown, that extends the length of the bowl-like surface. The pressure bar 600 is utilized by applying the surface of the pressure bar 600, particularly the protrusion 620, next to the wound or wound pad. The protrusion 620 of the pressure bar 600 is preferably applied to the wound pad in order to apply sufficient pressure to control bleeding. The bandage is then wrapped around the wound.

The pressure bar 600 further includes flaps 640 for attaching the pressure bar 600 to the bandage. The flaps 640 may also include attachment means for attaching the pressure bar 600 to the bandage 610. These attachment means may include, for example, stitching, Velcro®, clips or other attachment means. The flaps 640 may also be made of a resilient material that provides additional support and rigidity to the pressure bar 600.

FIGS. 7(a)-(d) and 8(a)-(d) illustrate exemplary embodiments of fasteners that may be used with the present invention. FIG. 7(a) illustrates a front view of a retainer clip fastener 760 formed of two hinged members 762, 764. The hinged members include a perimeter member 762 and an interior member 764. The hinged members are coupled together at a hinged end 766 and separate at an open end 768, as illustrated in side view FIG. 7(b). The hinged end provides a certain amount of tension between the two separable hinged members 762, 764. The fastener 760 works by inserting the open end 768 over a wrapped bandage 710, as illustrated in FIGS. 7(c) and (d). The tension provided by the hinged members 762, 764 helps secure the bandage and prevents unraveling. One or several retainer clip fasteners 760 may be used to secure the bandage 710.

FIG. 8(a) illustrates a side view of an E-clip fastener 860 that may be used with the present invention. The E-clip fastener 860 is formed of a thin back member 862 having three or more teeth members 864 that project from the back member 862. The E-clip fastener 860 works by inserting the teeth into a wrapped bandage 810, as illustrated in FIG. 8(d). At least one of the teeth members 864 includes a hook 866 that attaches to the bandage 810. The teeth members 864, including hook(s) 866, help secure the bandage and prevent unraveling. One or several E-clip fasteners 860 may be used to secure the bandage 810.

Although the present invention has been described in terms of particular preferred and alternative embodiments, it is not limited to those embodiments. Alternative embodiments, examples, and modifications which would still be encompassed by the invention may be made by those skilled in the art, particularly in light of the foregoing teachings.

Those skilled in the art will appreciate that various adaptations and modifications of the preferred and alternative embodiments described above can be configured without departing from the scope and spirit of the invention. Therefore, it is to be understood that, within the scope of the appended claims, the invention may be practiced other than as specifically described herein.

VII. INDUSTRIAL APPLICABILITY

The above-described invention is useful for the treatment and dressing of wounds by reducing the time required to treat and dress a wound. The invention is particularly useful in providing means for quickly controlling bleeding in situations where there are limited treatment materials or where time is vital.

I claim:

1. A wound dressing system, comprising:
   an elongated elastic wrap;
   a receptacle attached to said wrap, said receptacle comprising a pocket, the pocket including an exterior surface adapted for contact with a wound, the exterior surface including a layered structure comprising a non-adherent pad formed as a wound pad and suitable for placing directly on a wound;
   a treatment material being removably disposed inside said receptacle, said receptacle including an exit to facilitate removal of said treatment material and, at least one substantially rigid pressure member in communication with said wrap.

2. The wound dressing system of claim 1, wherein the layered structure comprises a plastic layer adjacent the non-adherent pad.

3. The wound dressing system of claim 2, wherein said plastic layer forms an occlusion barrier.

4. The wound dressing system of claim 1, wherein said treatment material comprises a sterilized woven fabric or gauze.

5. The wound dressing system of claim 1, wherein said treatment material includes a blood coagulant.

6. The wound dressing system of claim 1, wherein said treatment material includes a medicament.

7. The wound dressing system of claim 1, wherein said wrap comprises an elastic bandage.

8. The wound dressing system of claim 1, wherein said receptacle is fixedly attached to said wrap.

9. The wound dressing system of claim 1, wherein said receptacle is removably attached to said wrap.

10. The wound dressing system of claim 1, wherein said receptacle is adjacent to and is capable of being detached from said bandage.

11. The wound dressing system of claim 1, wherein said wrap includes at least one fastener disposed on at least one surface.

12. The wound dressing system of claim 11, wherein said at least one fastener comprises a plurality of spaced strips.

13. The wound dressing system of claim 12, wherein said strips comprise hook and loop fasteners or adhesive.

14. The wound dressing system of claim 1, wherein said pressure member includes at least one arcuate or bowl-like surface that applies pressure to a wound.

15. A method of applying the wound dressing system of claim 1 to a wound, comprising:
    removing the treatment material from the receptacle;
    directly contacting the wound with the treatment material; and,
    contacting the treatment material with the wrap.

16. The method according to claim 15, further comprising:
    contacting the treatment material with said pressure member prior to contacting the treatment material with the wrap.

17. An integrated wound dressing system, comprising:
    a bandage suitable for dressing a wound;
    a receptacle attached to said bandage, said receptacle comprising:
        a wound contacting surface including a layered structure;
    at least one rigid pressure member in communication with said bandage; and,
    a treatment material disposed inside said receptacle, said receptacle including an exit to facilitate removal of said treatment material.

18. The wound dressing system of claim 17, wherein said layered structure comprises at least one of a non-adherent pad or a plastic layer.

19. The integrated wound dressing system of claim 17, further comprising a plastic layer disposed inside said receptacle.

20. The integrated wound dressing system of claim 17, wherein said receptacle includes an exit and said treatment material is folded within said receptacle such that said treatment material is controllably removable from said receptacle through said exit opening.

21. The integrated wound dressing system of claim 17, wherein said treatment material comprises a sterilized woven fabric or gauze.

22. The integrated wound dressing system of claim 17, wherein said treatment material includes a blood coagulant.

23. The integrated wound dressing system of claim 17, wherein said treatment material includes a medicament.

24. The wound dressing system of claim 17, wherein said receptacle is fixedly attached to said bandage.

25. The wound dressing system of claim 17, wherein said receptacle is removably attached to said bandage.

26. The wound dressing system of claim 17, wherein said receptacle is adjacent to and is capable of being detached from said bandage.

27. The integrated wound dressing system of claim 17, wherein said bandage includes at least one fastener disposed on at least one surface of said bandage.

28. The wound dressing system of claim 17, wherein said pressure member includes at least one arcuate or bowl-like surface that applies pressure to the wound.

29. A method of applying the wound dressing system of claim 17 to a wound, comprising:
    removing the treatment material from the receptacle;
    directly applying the treatment material to the wound;
    applying the pressure member to the wound via the treatment material; and,
    applying the bandage to the wound via the pressure member.

30. The method according to claim 29, further comprising: applying the pressure member to the wound prior to applying the treatment material to the wound.

31. The method according to claim 30, wherein applying the pressure member to the wound includes urging the arcuate surface against the treatment material.

32. The method according to claim 30, further comprising: applying a plastic layer onto the treatment material.

33. An integrated wound dressing system, comprising:
a wound dressing bandage;
a receptacle attached to said bandage, wherein said receptacle is formed as a wound pad and is suitable for placing directly on a wound, said receptacle comprising:
   a wound contacting surface including a layered structure, said layered structure formed of a non-adherent pad or a plastic layer; and
   an exit opening;
at least one pressure member in communication with said bandage, wherein said pressure member includes at least one arcuate or bowl-like surface capable of applying pressure to the wound; and
a treatment material disposed inside said receptacle, wherein said treatment material is capable of being removed from said receptacle through said exit opening.

34. A method of applying a wound dressing system to a wound, the wound dressing system comprising an elastic bandage; a receptacle attached to the elastic bandage, the receptacle including an exterior surface defining a wound pad, the method comprising applying a pressure bar to the wound prior to contacting the wound with the exterior surface of the receptacle:
   directly contacting the wound with the exterior surface of the receptacle; and
   wrapping the elastic bandage about the receptacle so as to compress the receptacle against the wound.

35. The method of claim 34, further comprising applying a pressure bar to the receptacle prior to wrapping the elastic bandage about the receptacle.

* * * * *